United States Patent [19]

Aoyama

[11] Patent Number: 5,285,396
[45] Date of Patent: Feb. 8, 1994

[54] DEVICE FOR EVALUATING RACE HORSE PERFORMANCE BASED ON TEMPERATURE

[76] Inventor: Tadamasa Aoyama, Maison Takashima 403, 10-15 Daimachi, Kanagawa-ku, Yokohama, Kanagawa, Japan

[21] Appl. No.: 795,481

[22] Filed: Nov. 21, 1991

[30] Foreign Application Priority Data

Jan. 11, 1991 [JP] Japan .................... 3-12677

[51] Int. Cl.$^5$ .................... G01K 17/00; G01J 5/00
[52] U.S. Cl. .................... 364/557; 250/338.1; 128/664; 374/121
[58] Field of Search .................... 374/120, 137, 121; 128/664, 736; 250/338.1, 340; 364/413.01, 413.02, 413.03, 550, 557

[56] References Cited

U.S. PATENT DOCUMENTS

| | | | |
|---|---|---|---|
| 4,379,461 | 4/1983 | Nilsson et al. | 128/736 |
| 4,574,359 | 3/1986 | Ishizaka et al. | 364/557 |
| 4,788,427 | 11/1988 | LeRoy | 250/340 X |
| 4,874,253 | 10/1989 | Pompei et al. | 374/121 |
| 5,017,019 | 5/1991 | Pompei | 128/664 X |

*Primary Examiner*—Jack B. Harvey
*Assistant Examiner*—Eric W. Stamber
*Attorney, Agent, or Firm*—Rogers & Killeen

[57] ABSTRACT

A device for evaluating a plurality of race horses' readiness for a race by quantitatively assessing the horses' temperatures without contacting the horses, the evaluation being made prior to the race when the race horses may be viewed in a paddock area. The device may include an infrared sensor for measuring the horses' temperatures at least three times in a random sampling period, an arithmetic operator for calculating characteristics of those measurements such as the maximum, minimum and mean, and various differences among the measured temperatures, and a display for providing a visual comparison of the measured and calculated values. The device may also correct the measured temperatures for the distance from which temperature measurements were taken.

5 Claims, 2 Drawing Sheets

DEVICE FOR EVALUATING RACE HORSE PERFORMANCE BASED ON TEMPERATURE

BACKGROUND OF THE INVENTION

1. Field of the Invention

The present invention relates to a method and device for measuring the temperature of an organism to obtain data for estimating a condition of the organism by detecting far infrared rays radiated by organisms such as a race horse and the like.

2. Description of the Related Art

Estimation of whether a race horse gallops splendidly in a race has been performed on the basis of information about the pedigree, race experiences and the results of the last race, or the increase or decrease in the body weight of the horse. However, since the splendid galloping of a horse depends on the condition of the horse as well as the past results and pedigree of the horse, even a horse having real power does not sometimes gallop splendidly. The condition of a horse has been estimated by observing the horse taken with a person in a paddock with human eyes. The condition of a horse may be estimated by observing the color of the fur or the gloss of the fur with human eyes. This technique does not involve the objective data because of the subjectivity of the observing person; therefore these data cannot be substantially quantified or averaged so as to be utilized by a large number of people at the same time.

SUMMARY OF THE INVENTION

The present inventor thought out that organisms such as a horse and the like radiated far infrared rays depending on their condition. The object of the present invention is to provide a method and device for measuring such organisms to estimate their condition.

The method of the present invention comprises: measuring far infrared rays radiated by organisms such as a race horse and the like by using a far infrared rays-measuring means constituted mainly by a far infrared rays sensor at least three times in a random sampling period; and outputting in an appropriate display means the numeral values obtained from an arithmetic operation of the predetermined measurements such as the minimal value and the maximal value, or the above mentioned measurements together.

Thus the condition of a race horse before a race will be determined by the results obtained from an operation of the measurements in which a dose of far infrared rays radiated from each racing horse are measured. Therefore, the condition of racing horses which has been observed with eyes can be represented by objective numeral data, so the present method is convenient practically.

DETAILED DESCRIPTION OF THE PREFERRED EMBODIMENTS

The present invention will now be described by way of an example thereof. It should be noted that the example is presented for the illustration purpose only and should not be interpreted in any restrictive way. Furthermore, the present invention is illustrated by example according to the attended Figures.

Figure 1:
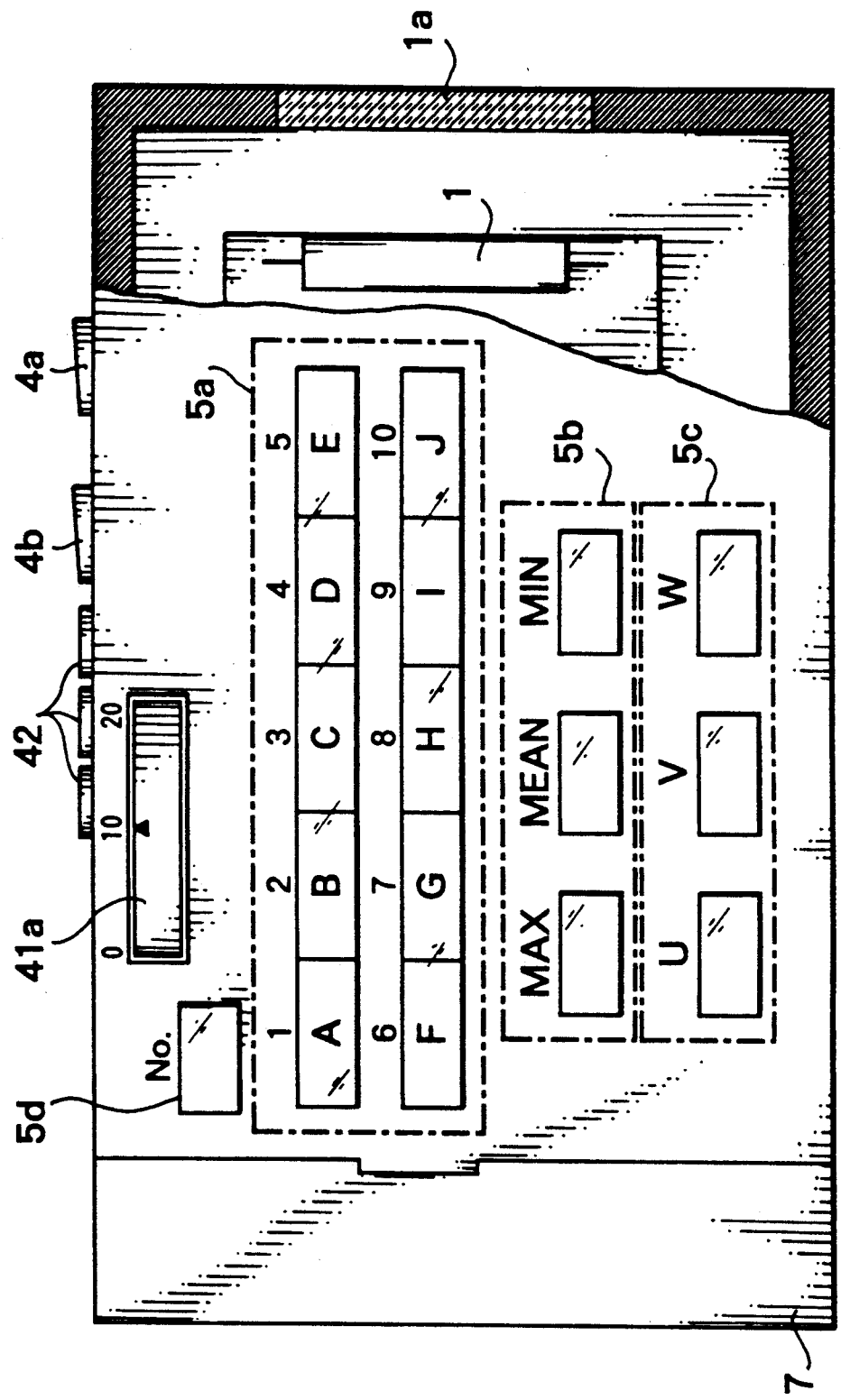
FIG. 1 is a partly diagrammatic sectional side elevation of an embodiment of the measuring unit for working the present invention.
Figure 2:
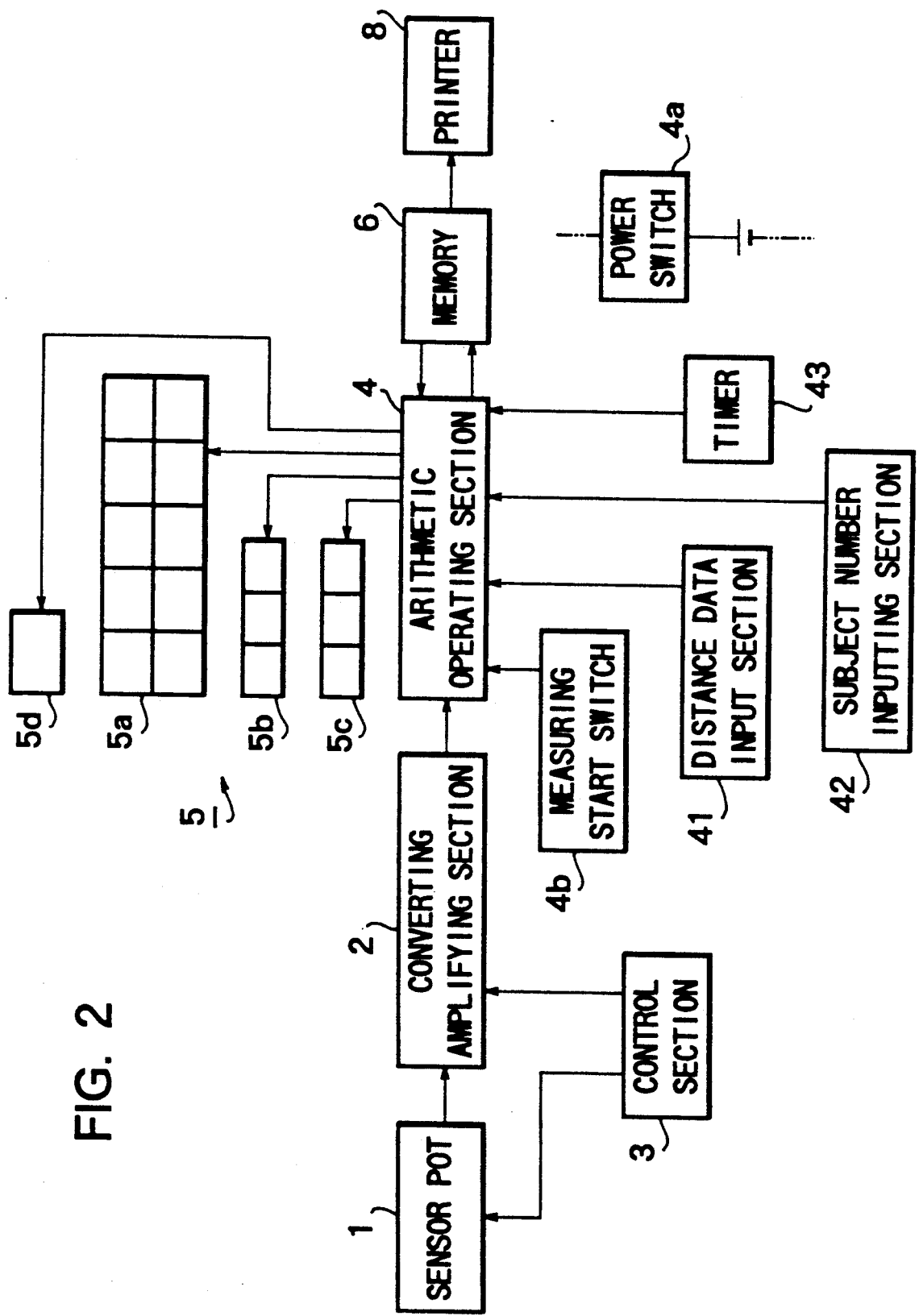
FIG. 2 is a block diagram shown in FIG. 1.

FIG. 1 is a partly diagrammatic sectional side elevation of an embodiment of the measuring unit for working the present invention, and FIG. 2 is a block diagram.

A reference numeral "1" in FIG. 1 denotes a far infrared rays sensor pot, which, e.g., is constituted by a thermal detector. The detectors may be those which utilize quantum effects and a resonance detector. A reference numeral "1a" shows a mask filter, in which, if necessary, a quite freely opening and shutting shutter (not shown) may be provided.

Thus the above mentioned sensor pot 1 with a thermal detector convert the incident far infrared rays from a horse body to heat, which operates a generating means of a signal proportional to the received amount of thermal energy.

A reference numeral "2" in FIG. 2 denotes a converting-amplifying section which converts and amplifies the signal outputted from the above mentioned sensor pot 1 to a suitable electrical signal. In the section, far infrared rays generated in the above mentioned sensor pot 1 is converted to a digital signal and amplified.

A reference numeral "3" denotes a control section which controls the operation timing between the above mentioned sensor pot 1 and converting-amplifying section 2, and then a signal from the converting-amplifying section 2 is supplied to the next arithmetic operating section 4.

In the arithmetic operating section 4, each measurement from the converting-amplifying section in each operation is once stored in a memory 6 as it is, and then the measurement is read out so that it may be corrected by a correcting element such as a measurement distance and the like. The corrected value is supplied to a display section 5 to display each measurement, and then the corrected values are combined to treat on the basis of the predetermined plural arithmetic equations, the value from the treatment being supplied to the display section 5 to display the arithmetic operating value. The value after correction and the measurements from the arithmetic operation are also stored in the memory 6.

The above mentioned arithmetic operating section 4 is accompanied by a distance data input section 41 which corrects the variations of the measurements ascribed by change in the distance between the sensor pot 1 and an organism such as a horse as a subject, a subject number inputting section 42 which inputs the numbers of the subjects, and a time 43 which selects and changes the operation timing against the above mentioned control section 3.

Reference numerals "5a-5c" denote display sections in FIG. 1, in which ten display media with LED and the like to display plural measuring times, e.g., ten measurements, and six display media to display the measurements obtained from the arithmetic operation.

A reference numeral "5d" denotes a display section of a subject number, i.e., a proper number assigned to a horse as a subject, "41a" an input dial in the distance data inputting section 41, "4a" a power switch,, "4b" a measuring start switch, and "7" a power supply, these sections constituting a measuring unit used in the present invention.

Furthermore, an embodiment of the above mentioned unit is illustrated in the following.

When a race horse is taken with a person in a paddock in a race track, the power switch 4a is turned on, the distance between the measuring person and the measured point (location) is measured with eyes, and the distance input dial 41a is adjusted to the value of the distance measured with eyes.

If the sensor pot 1 in the measuring unit is turned toward the horse to be measured and the measuring start switch 4b is pushed, far infrared rays radiated from the horse is measured in a suitable sampling time period, e.g., a 200 msec sample taken at least three times in a random sampling period and preferably ten times successively.

Measurement is performed in the above mentioned predetermined time period, and then 10 measurements after sampling are displayed in the above mentioned 10 display media with or without correction.

For example, each of the 10 measurements are subjected to arithmetic operation in the arithmetic operating section 4 as follows.

First, the maximal value (Max), the minimal value (Min) and the mean value (Mean) are displayed at the display 5b in the display section 5, respectively.

Then, the difference (absolute value) between the sum of the first measurement A and fourth measurement D and the sum of the fifth measurement H and the eighth measurement H is operated in the arithmetic operating section 4, and the obtained value U is displayed in the display 5c in the display section 5.

The difference V between Max and Min is obtained from the operation, and then the difference W between Mean and V is also obtained from operation, values V and W are each displayed in the display 5c in the display section 5.

Each value U, V and W obtained from the operation in the arithmetic operating section is stored in the memory 6. The display means may be the other visual display means such as an analog meter display or an on and off display of the LED line besides the digital display. Furthermore, the measuring order and number of each horse is displayed in the display section 5d, which is stored in the memory 6 together with the measurements in each time already stored in the memory 6.

Thus for example, the plural race horses which pass the measuring point in the paddock successively are measured for the amount of far infrared rays radiated from them.

Although each measurement measured in each race horse is displayed in each display section 5a–5c for each measurement A–J and the predetermined arithmetic operation value U, V and W of each horse in every measuring, when each measurement and arithmetic operation value of each horse stored in the memory is to be displayed lately, an operation switch in the memory 6 may be put on to display the value in the display section 5a–5d. The each measurement may also be printed out, if a printer 8 is provided in the unit.

The thus obtained measurements and arithmetic operation values on each horse are evaluated on the basis of much experienced results as follows.

That is, good evaluation is that the value $|U|$ obtained from the above mentioned arithmetic equation, $(A+D)-(E+H)=|U|$, is less; the value V obtained from the equation, $Max-Min=V$, is also less; and the value W obtained from the equation, $Mean-V=W$, is also less at a sampling period of 200 msec in a total of 10 times of measuring one horse. These results are based on the experience that a horse whose value of far infrared rays obtained in plural measurings at an appropriate sampling period is not varied and stable has exerted a splendid galloping.

When a betting ticket to a race horse was bought according to the above mentioned evaluation standard, a probability involved in the repayment prize (Rensho Hukushiki) was 80% or more.

We claim:

1. A device for remotely measuring the relative readiness of a plurality of race horses for a race comprising:
    an infrared sensor for remotely measuring a race horse's temperature by sensing infrared radiation from the horse without contacting the horse
    and for taking at least three temperature measurements of the horses that are to be in a race prior to the race;
    a memory for storing all of the measured temperatures;
    an arithmetic operator for (a) correcting the stored temperature measurements for the distance from which the temperature measurements were made,
    and (b) determining for each of the horses from which temperature measurements have been taken, the maximum, minimum and mean corrected temperature measurements; and
    a display for displaying for each of the horses from which measurements have been made, all of the corrected measured temperatures, and the maximum, minimum and mean corrected temperature measurements
    so that the displayed measurements can be visually compared to evaluate the horses' readiness for the race.

2. The device of claim 1 wherein said arithmetic operator further determines for each of the horses from which measurements have been made;
    the absolute value of the difference U between (a) the sum of two of a first set of plural temperature measurements and (b) the sum of two of a subsequent set of plural temperature measurements,
    the difference V between the maximum and minimum measured temperatures, and
    the difference W between the mean of the measured temperatures and V.

3. The device of claim 2 wherein said display further displays the differences U, V and W, and wherein said visual comparison is further based on the differences U, V and W with the horses having the lowest values U, V and W being likely to be at a higher state of readiness for the race than the other horses.

4. The device of claim 2 wherein said infrared sensor takes and said memory is able to store ten temperature measurements of each of the horses.

5. The device of claim 4 wherein the value U determined by said arithmetic operator is the absolute value of the difference between the sum of the first and fourth temperature measurements and the sum of the fifth and eighth temperature measurements.

* * * * *